United States Patent [19]

Kurakake

[11] Patent Number: 5,059,799
[45] Date of Patent: Oct. 22, 1991

[54] SCINTILLATION CAMERA

[75] Inventor: Tadakazu Kurakake, Tochigi, Japan

[73] Assignee: Kabushiki Kaisha Toshiba, Kawasaki, Japan

[21] Appl. No.: 502,031

[22] Filed: Mar. 30, 1990

[30] Foreign Application Priority Data

Apr. 4, 1989 [JP] Japan ................................ 1-85358

[51] Int. Cl.$^5$ .............................................. G01T 1/20
[52] U.S. Cl. .......................... 250/363.1; 250/363.08; 250/363.02
[58] Field of Search .............. 250/347, 363.10, 363.08, 250/363.02

[56] References Cited

U.S. PATENT DOCUMENTS

| 4,109,155 | 8/1978 | Tschunt et al. | 378/148 |
| 4,629,893 | 12/1986 | Hanz et al. | 250/363.10 |
| 4,692,625 | 9/1987 | Hanz et al. | 250/363.08 |
| 4,758,726 | 7/1988 | Douma et al. | 250/363.10 |

FOREIGN PATENT DOCUMENTS

| 0156112 | 10/1985 | European Pat. Off. | 250/363.1 |
| 57-161575 | 10/1982 | Japan |  |
| 59-180476 | 10/1984 | Japan | 250/363.1 |
| 60-165568 | 8/1985 | Japan | 250/363.1 |

Primary Examiner—Constantine Hannaher
Assistant Examiner—Jacob M. Eisenberg
Attorney, Agent, or Firm—Cushman, Darby & Cushman

[57] ABSTRACT

A scintillation camera comprises a gantry having a plurality of detectors, and a plurality of sections which are assigned to the respective detectors, and to which a plurality of collimators are intended to be attached. A carrier simultaneously supports the collimators to attach them to their attaching-sections respectively, while the carrier simultaneously supports the collimators which have been attached to their attaching-sections, to detach them therefrom. The attaching or detaching of plural collimators can be simultaneously done by only one carrier. Therefore, the time needed to change the collimators can be decreased and the operation of changing them can be made extremely easier. As the result, the efficiency of changing them can be greatly enhanced.

14 Claims, 7 Drawing Sheets

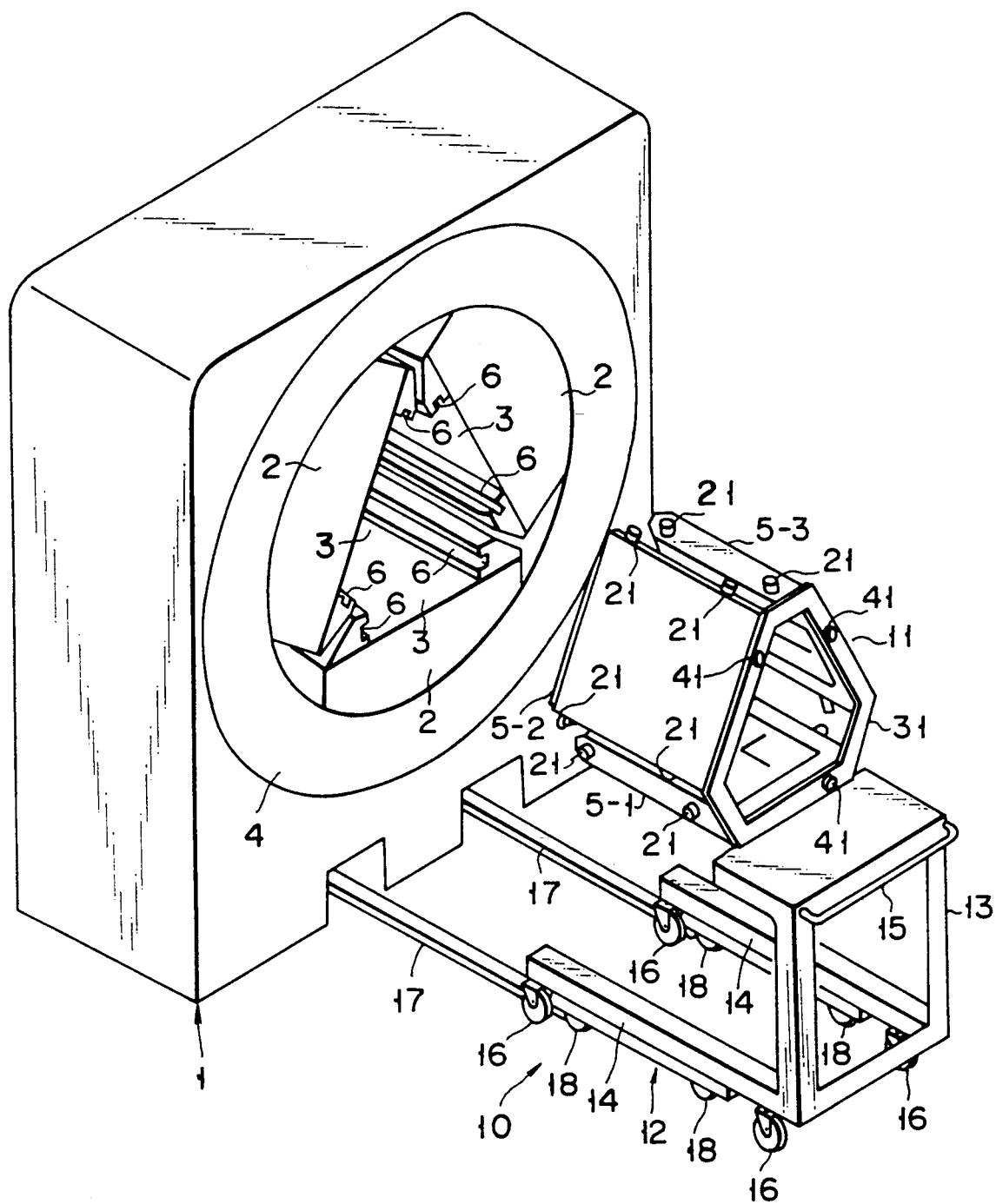
F I G. 1

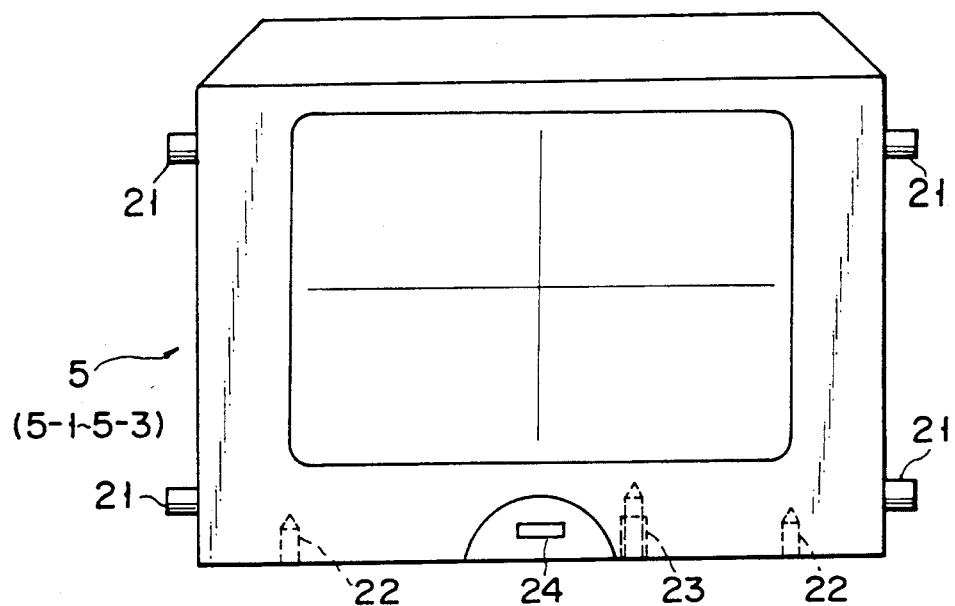
F I G. 4A
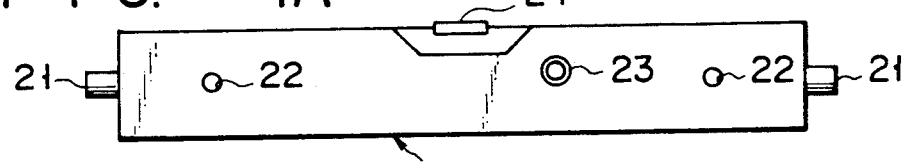
F I G. 4B
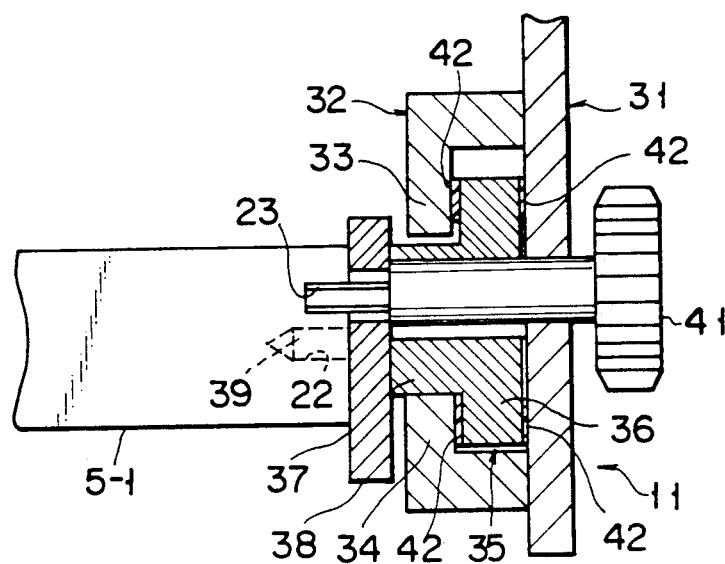
F I G. 5

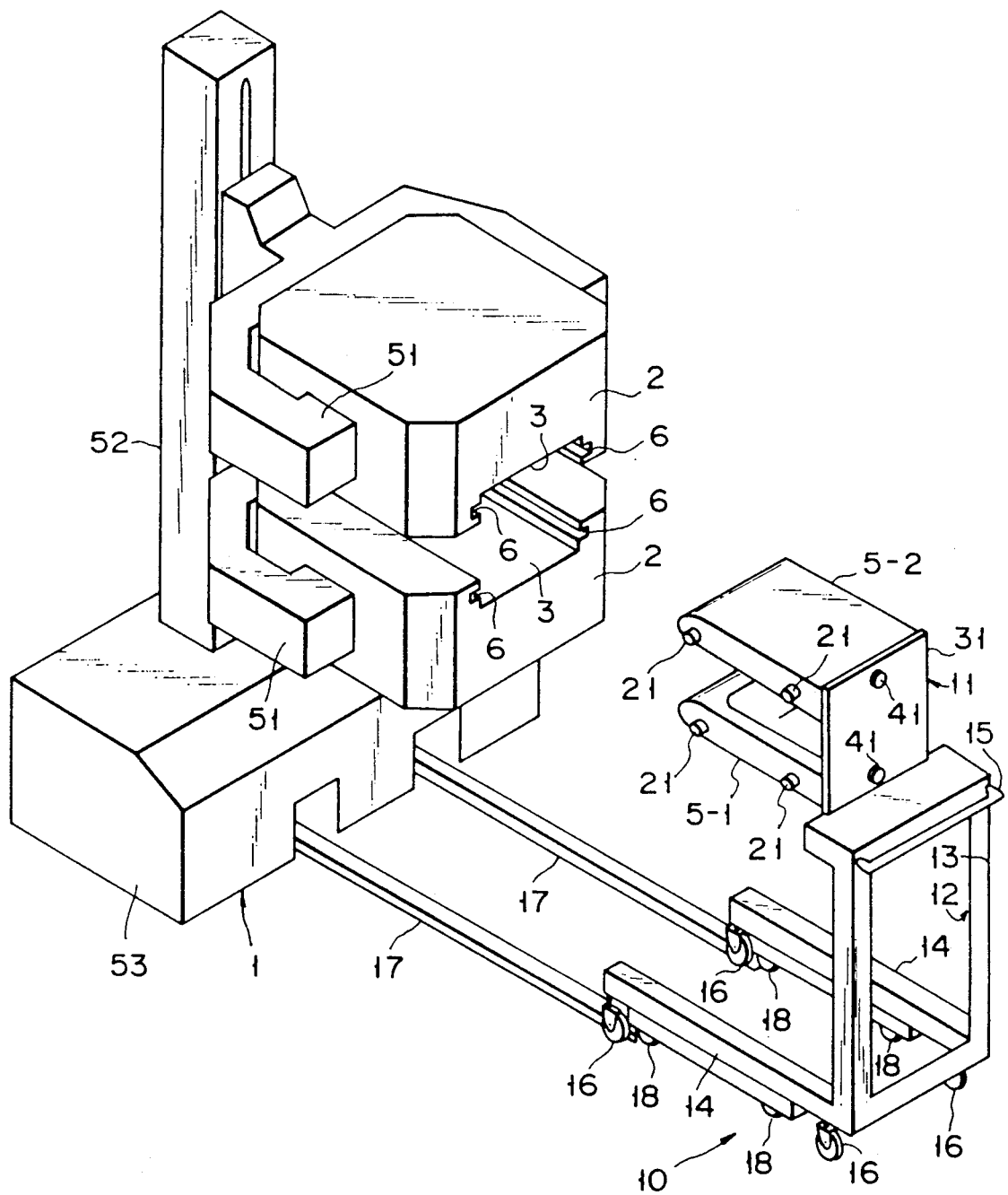
F I G. 8

SCINTILLATION CAMERA

BACKGROUND OF THE INVENTION

1. Field of the Invention

The present invention relates to a scintillation camera for radiographing the two-dimensional distribution image or tomographic image in accordance with radioactive isotope distributed in an examined body, and more particularly, relates to a scintillation camera including a carrier for exchanging collimators attached to detectors.

2. Description of the Related Art

In the case of the detector attached to the scintillation camera, gamma rays radiated from the examined body interact in the scintillator, and fluorescent rays proportional to their absorption energy are emitted from the scintillator. The fluorescent rays are received by the photomultiplier tube and electric pulses proportional to the amount of fluorescent rays are output. The pulses output are signal-processed to form the two-dimensional distribution image or tomographic image.

The detector includes a collimator opposed to the examined body and located in front of the scintillator. The collimator is a plate made of lead and formed with a plurality of holes. The collimator serves to introduce those gamma rays, which are radially radiated from the examined body and which are parallel to its holes, to the scintillator, while the collimator serves to shield the other gamma rays which are radiated obliquely to the collimator's holes. The collimators are grouped to use for high, medium and low energies, depending upon the energies of radioactive isotope. They are also grouped according to sizes of their holes, because resolution and sensitivity of images change depending upon the sizes of their holes. Therefore, various kinds of collimators are available and they must be selected to meet the purposes of radiographing. In other words, they must be changed every time when radiographing purposes change.

Conventionally, one scintillation camera usually includes one detector and one collimator. Only one collimator is exchanged with another, every time radiographing purposes change, so that the exchanging operation is carried out by hands or by a carrier and is quite easy.

However, scintillation cameras have recently been developed which have high qualities, one type of which has plural (more concretely, three or four) detectors. Since one detector needs to have one collimator, plural collimators must be attached to one scintillation camera. When radiographing purposes change, therefore, plural collimators must be exchanged with other ones. When the collimators are exchanged with other ones one by one by hand or by the carrier, as usually seen in the conventional cases, quite a long period of time is required and the efficiency of exchanging operation is quite low.

SUMMARY OF THE INVENTION

The object of the present invention is to provide a scintillation camera with plural detectors, capable of simultaneously exchanging all of plural collimators in order to significantly increase the efficiency of collimator-exchange operation.

According to the present invention, there is provided a scintillation camera comprising:

a gantry having a plurality of detectors, and a plurality of sections which are assigned to the respective detectors, and to which a plurality of collimators are intended to be attached;

a carrier for simultaneously supporting the collimators to attach them to their attaching-sections respectively, and for simultaneously supporting the collimators which have been attached to their attaching-sections, to detach them therefrom.

According to the present invention, the attaching or detaching of plural collimators can be simultaneously done by only one carrier. Therefore, the time needed to change the collimators can be decreased and the operation of changing them can be made extremely easier. As the result, the efficiency of changing them can be greatly enhanced.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a perspective view showing an example of the scintillation camera according to the present invention;

FIGS. 4A and 4B are plan and side views showing the collimator;

FIGS. 5 and 6 are sectional views showing a support of the carrier;

FIG. 8 is a perspective view showing another example of the scintillation camera according to the present invention.

DETAILED DESCRIPTION OF THE PREFERRED EMBODIMENTS

Figure 2:
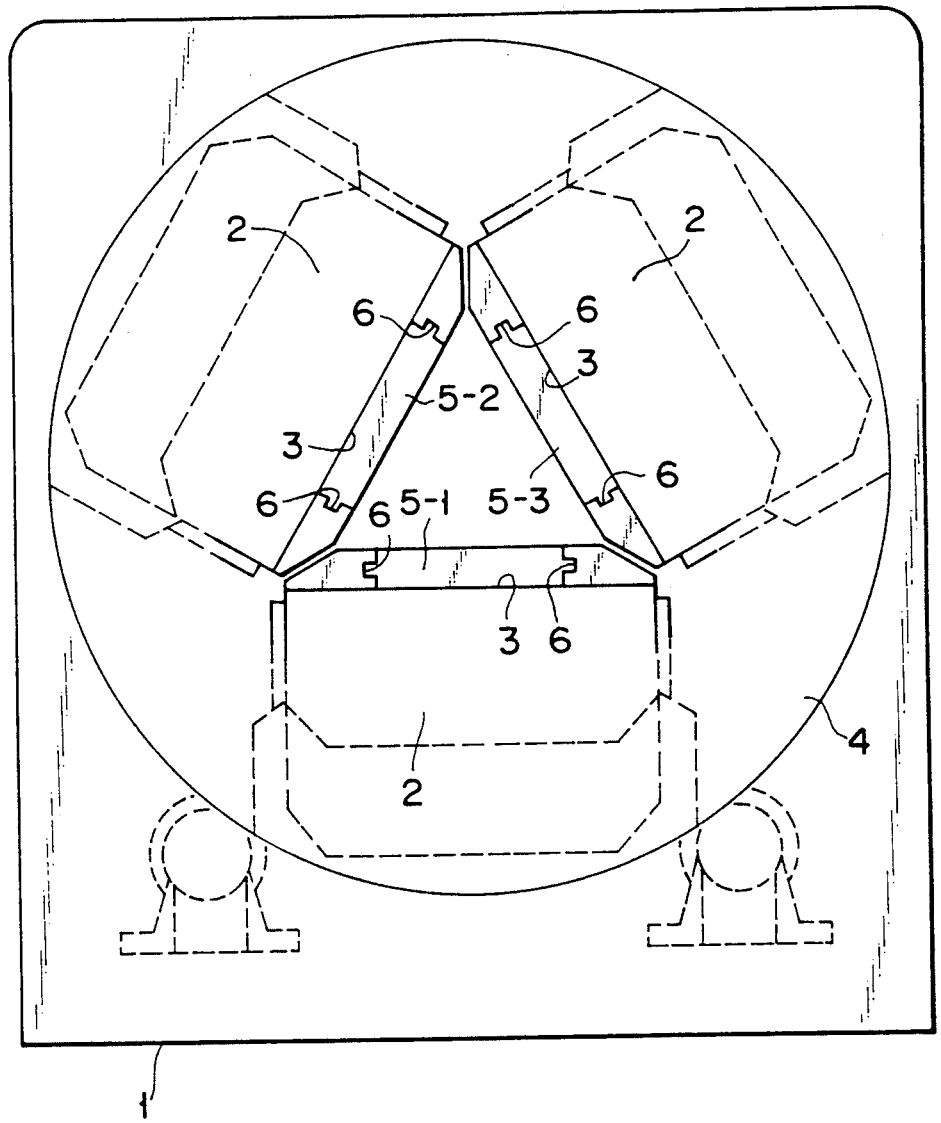
FIG. 2 is a front view showing the gantry for the scintillation camera shown in FIG. 1.

FIG. 1 shows gantry 1 and carrier 10 for an example of the scintillation camera according to the present invention. Carrier 10 which supports three collimators 5-1, 5-2 and 5-3 is pushed toward collimators-attaching sections 3 of detectors 2 in gantry 1 to simultaneously attach the collimators thereto. On the other hand, three collimators 5-1, 5-2 and 5-3 which have been attached to collimators-attaching sections 3 of detectors 2 are supported by carrier 10 and then pulled out of gantry 1 by carrier 10 so as be to simultaneously detached therefrom. In short, three collimators 5 can be simultaneously exchanged with new ones by carrier 10.

As shown in FIGS. 1 and 2, gantry 1 is provided with a rotation system which includes rotating ring 4. Three detectors 2 are attached to rotating ring 4 and can move in the radial direction of ring 4. A scintillator, a photomultiplier tube (both not shown) and the like are housed in each of detectors 2.

The housing of each of detectors 2 has section 3 to which each collimator 5-1, 5-2 and 5-3 is attached. Collimator-attaching section 3 is provided with guide grooves 6 for allowing pins 21 of the collimator to be introduced thereinto. Pins 21 and guide grooves 6 define means for guiding the collimator.

Carrier 10 comprises support 11 for supporting collimators 5, and section 12 for carrying the support.

Figure 3:
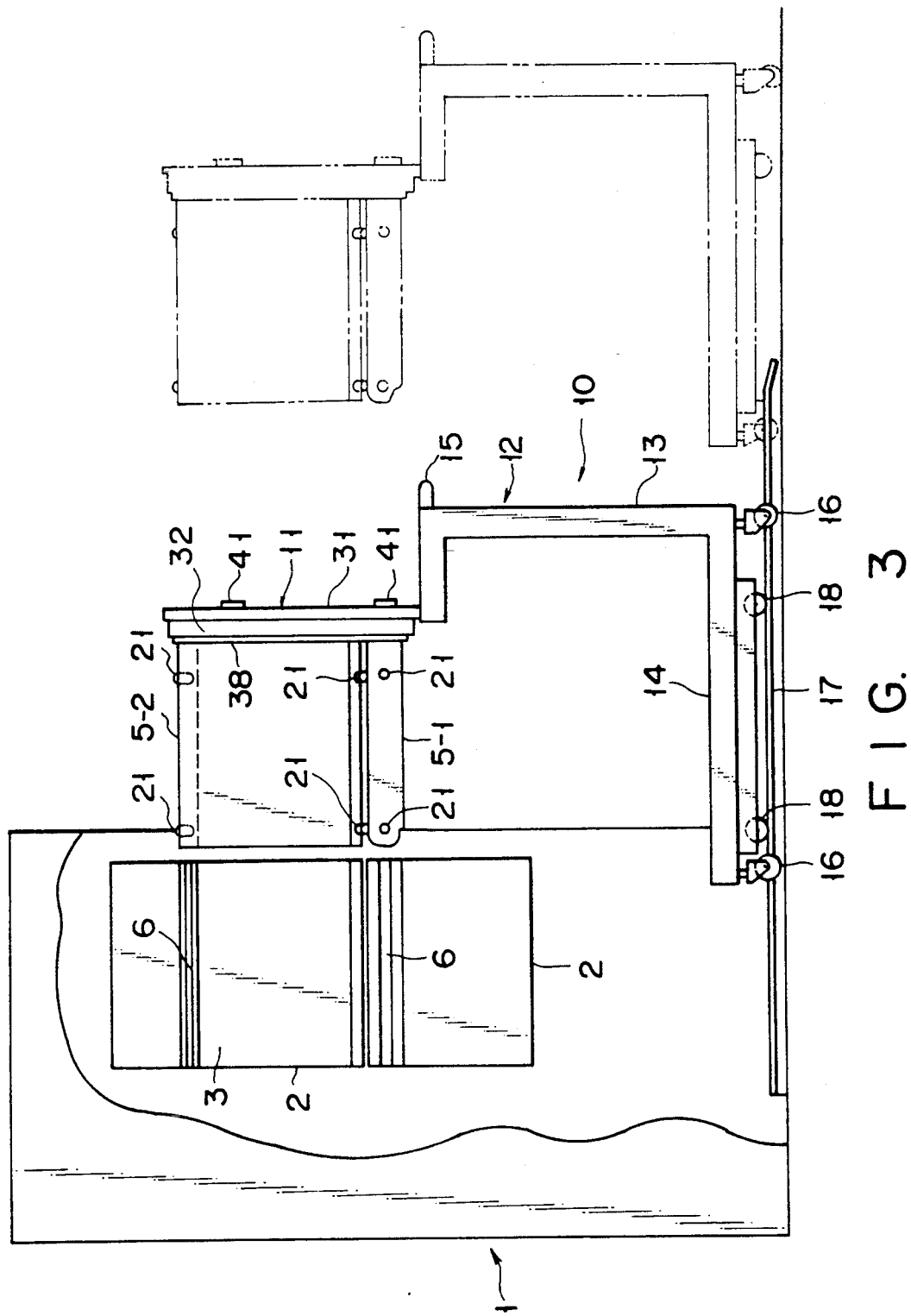
FIG. 3 is a side view (partly sectioned) showing the gantry and the carrier in FIG. 1.

Carrying section 12 comprises frame-like body 13, wheel supports 14 extending horizontally, and handle 15 attached to body 13. First wheels 16 for running on the floor are attached to wheel supports 14. Rails 17 are solid enough to support the carrier and they are extended from the gantry in order to meet the levels between the gantry and the carrier. As will be described later, rails 17 are intended to align pins 21 of the collimator with guide grooves 6, even when the floor is uneven. Second wheels 18 for running on rails 17 are further attached to wheel supports 14. As shown in FIG. 3, second wheels 18 are attached higher than first wheels 16. When second wheels are riding on rails 17, the distance extending from the top of rail 17 to the longitudinal center line of each guide groove 6 is set at a predetermined value.

Accordingly, as shown in FIG. 3, when carrier 10 runs with its first wheels 16 rolled on the floor and its second wheels 18 ride on rails 17, first wheels 18 are separated from the floor and carrier 10 runs with its second wheels 18 rolled on rails 17.

When carrier 10 is carried onto rails 17 first with its first wheels 16 touched on the floor and then with its second wheels 18 touched on rails 17, as shown in FIG. 3, therefore, first wheels 16 are separated from the floor while second wheels 18 run on rails to carry carrier 10. The floor in the detecting room is usually uneven but the rails 17 are extended from the gantry so that rails 6 and 17 are set parallel. When second wheels 18 run on rails 17, the posture of carrier 10 can be made horizontal, without the unevenness of the floor, so that the height of the collimator can be accurately aligned with that of its corresponding collimator-attaching section 3.

As shown in FIGS. 4A and 4B, each collimator is provided with four pins 21 to be engaged with guide grooves 6. Each collimator may be provided with six pins. Further, each collimator is provided with pin holes 22 and screw hole 23. It is further provided with screw 24 for fixing it to its attaching section 3 when it is finally attached to this section 3.

Figure 6:
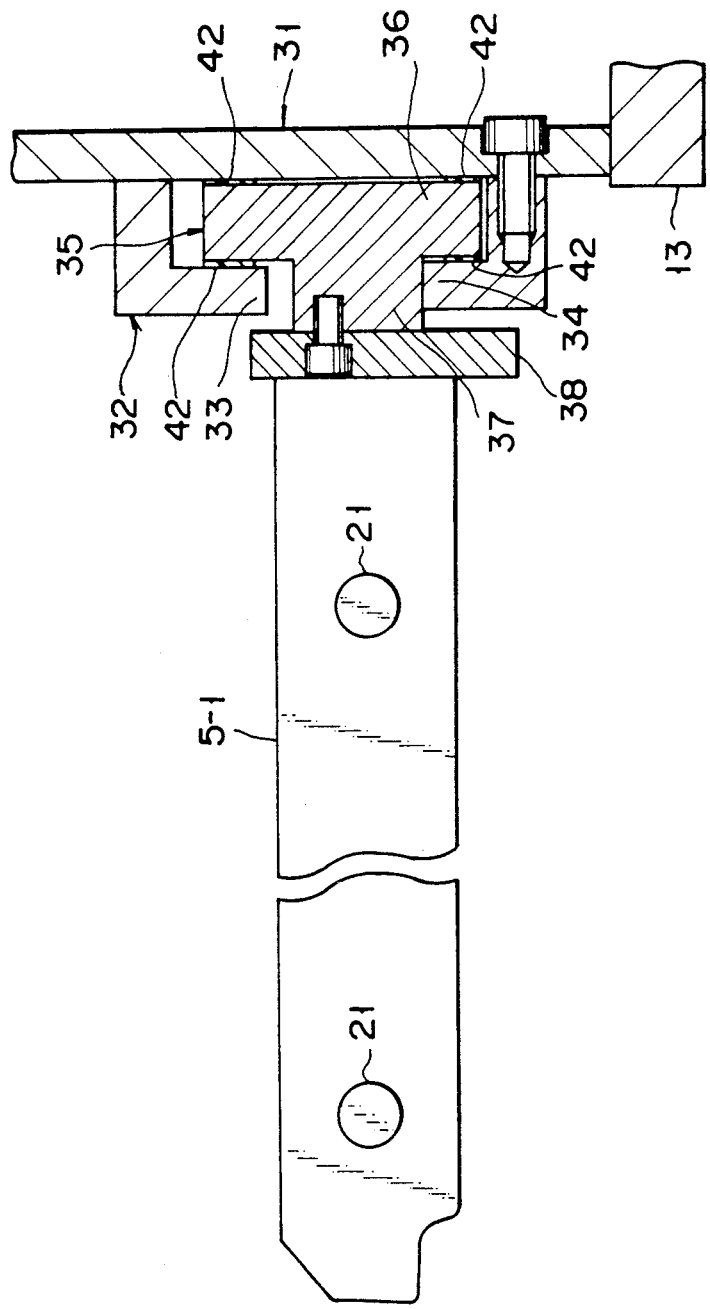

As shown in FIGS. 1 and 2, support or support section 11 of carrier 10 includes substantially triangular (or hexagonal) support frame 31 vertically erected. As shown in FIGS. 5 and 6, first block 32 is fixed to this support frame 31. First block 32 comprises upper and lower halves 33 and 34. Second block 35, movable up and down, is arranged in first block 32 and it comprises long and short sectional parts 36 and 37. Plate 38 is contacted with short sectional part 37 of movable block 35 and the base of collimator 5-1 is contacted with this plate 38 by screw 41. Pins 39 projected from plate 38 are fitted into pin holes 22 of collimator 5-1, so as to support collimator 5-1. Further, attaching screw 41 is screwed into screw hole 23.

Support section 11 is further provided with a system for supporting collimator 5-1 so as to be movable vertically, horizontally and in its rotating direction.

As shown in FIG. 5, the left-side surface of support frame 31 and the right-side surfaces of upper and lower halves 32 and 33 of first block 32 are formed so as to have extremely low surface roughness. Sliding members (or sliders) 42 are bonded to both sides of long sectional part 36 of movable block 35. Sliders 42 are pressed against the left-side surface of support frame 31 and the right-side surfaces of upper and lower halves 32 and 33. Therefore, almost no frictional force occurs between sliding members 42 and these surfaces of frame and block. Collimator 5-1 and block 35 can thus move vertically, horizontally and in their rotating direction. As the result, of gravity acting on them, they are usually tend to move downward, thus their short sectional part 37 comes into contact with lower half 34 of first block 32. Collimator 5-1 is therefore supported by support section 11 under such a state that it is usually shifted in the direction of gravity.

Figure 7:
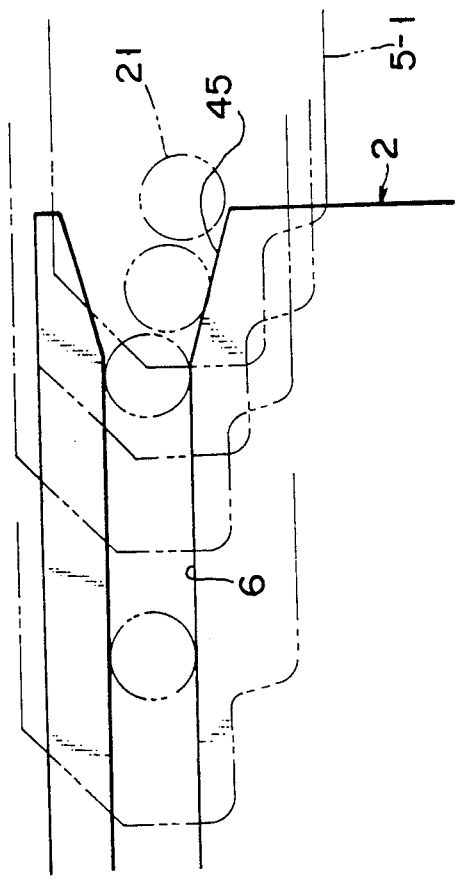
FIG. 7 is intended to explain how pins of the collimator are guided into grooves at the collimator-attaching section.

As shown in FIG. 7, tapered area 45 is formed at the entrance of each of guide grooves 6 in collimators attaching sections 3.

As shown by two-dot and dash lines in FIG. 7, when collimator 5-1 reaches the entrance of its attaching section 3 and carrier 10 is further pushed into gantry 1, pins 21 of collimator 5-1 slide on tapered area 45 into guide grooves 6. When pins 21 are guided on tapered area 45, collimator 5-1 is lifted. In other words, pins 21 and tapered area 45 form a means for lifting the collimator. Collimator 5-1 is thus moved in the horizontal and rotating directions. The position of the collimator can be thus adjusted in relation to the collimator-attaching section. Therefore, the collimator supporting system and lifting means cooperate to serve as a means for adjusting the position of the collimator relative to the collimator-attaching section.

The collimator may be sometimes shifted from its attaching section vertically as well as horizontally and in the rotating direction, because the collimator-attaching section 3 is a little wrongly incorporated in the gantry, the detectors are stopped, a little shifting from their predetermined positions, or any of the collimators-attaching sections is bent loose. In such a case, collimator's position relative to its attaching section can be automatically adjusted by pushing carrier 10 into the gantry, so that it can be correctly and accurately attached to its attaching section.

The amount by which the collimator is lifted is set to meet the maximum positional shift of the collimator relative to the collimator-attaching section, and this enables the collimator to be correctly attached to its attaching section.

Only first collimator 5-1 which is horizontally supported by the support section of carrier 10 is shown in FIGS. 5 through 7, but needless to say, those areas which are tapered in the direction of gravity are also formed at the entrance of guide grooves 6 for second and third collimators 5-2 and 5-3 which are obliquely supported.

It will be described how the collimators are attached to their attaching sections. Collimators 5 are stored while being supported by carrier 10. This carrier 10 is carried toward gantry 1 and second wheels 18 of carrier 10 run on rails 17. Carrier 10 is thus leveled to keep each of the collimators at its predetermined height.

When carrier 10 is further moved on rails 17, pins 21 of collimators 5 meet tapered areas 45 of guide grooves 6 and slide there-into. When pins 21 are guided on tapered areas 45, collimators 5 are lifted and moved in the horizontal and rotating directions, thereby adjusting their positions relative to their attaching sections.

Pins 21 are successively pushed into guide grooves 6 and collimators 5 are guided to their predetermined positions. Attaching screws 41 are then loosened to detach collimators 5 from carrier 10, while fixing screws 24 are tightened to fix collimators 5 to their attaching sections 3. Carrier 10 is returned to its original position and the attaching of collimators 5 is thus completed.

It will be described how the collimators are detached from their attaching sections in the pedestal. Carrier 10, while not supporting any collimators, is moved to its predetermined position in gantry 1, running on rails 17. Pins 39 of carriers 10 are inserted into pin holes 22 of collimators 5 and attaching screws 41 are tightened to support collimators 5 on carrier 10, while fixing screws 24 are loosened to detach collimators 5 from their attaching sections 3. Carrier 10 is pulled out of gantry 1, running on rails 17, and then moved to its storage place by wheels 16. The detaching of the collimators is thus completed.

The collimators are stored under such a state that they are supported by the carrier. This makes it unnecessary to store them on storage shelves. The process of transferring them from the carrier to the storage shelves is thus made redundant.

A second embodiment of the present invention will be described referring to FIG. 8.

This second embodiment relates to a stand type scintillation camera, i.e., such type that keeps detectors 2 not rotated. Bones in the entire human body and the like can be radiographed in this case. Two detectors 2 are supported by U-shaped arm members 51, which are supported, movable up and down, by vertical member 52. This vertical member 52 is erected on base member 53. Two collimators 5-1 and 5-2 are supported by support frame 31 of carrier 10.

In this case, too, rails 17 are prepared to level the carrier, each of detectors 2 is provided with guide grooves, each of guide grooves 6 is tapered at its entrance. Carrier 10 is provided with the system (not shown) for supporting the collimators movable in the vertical, horizontal and rotating directions. Therefore, this second embodiment can achieve same merits as the first embodiment.

As apparent from the above, the present invention can be applied to scintillation cameras of the stand type that support the detectors not rotated, as well as those of the type that support the detectors rotatable round the human body. Whichever type they may belong to, therefore, the present invention can be applied to all of those scintillation cameras which has at least two detectors.

According to the present invention, the attaching or detaching of plural collimators can be simultaneously done by only one carrier. Therefore, the time needed to change the collimators can be decreased and the operation of changing them can be made extremely easier. As the result, the efficiency of changing them can be remarkably enhanced.

Further, the second wheels are supported on the rails, so that although the floor may be, uneven each of the collimators can be leveled to accurately match the height of its attaching section in the gantry.

Furthermore, each of the collimators is provided with pins, while its attaching section is provided with guide grooves into which the pins are introduced, thereby enabling the collimator to be more easily guided into its attaching section.

Still further, the system for supporting the collimators movable in their vertical, horizontal and rotating directions is provided to support the collimators in such a way that they are usually shifted by a predetermined amount in the direction of gravity. In addition, each of the guide grooves of the collimators-attaching sections is tapered at its entrance and in the direction of gravity. This enables the position of each of the collimators to be automatically adjusted relative to its attaching section when the carrier is pushed toward the collimators-attaching sections. In the case where the collimator is shifted in position from its attaching section (in the vertical, horizontal and rotating directions), therefore, it can be accurately and surely attached to its attaching section.

Still further, the support system is quite simple in structure, which simplifies production and decreases manufacturing costs.

In addition, the collimators are stored while being supported by the carrier. The operation of transferring the collimators from the carrier to storage shelves can be made unnecessary.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A scintillation camera system comprising:
   a scintillation camera comprising:
      a plurality of detectors, the plurality of detectors being arranged to provide an opening for allowing an object such as a human to be inserted into the scintillation camera;
      a plurality of collimators, each collimator corresponding to one of the detectors; and
      means, associated with each of the detectors, for removably securing each collimator to a corresponding one of the detectors; and
   carrier means, movable in a direction substantially normal to the opening, for simultaneously inserting the plurality of collimators into the opening of the scintillation camera and simultaneous attaching each of the plurality of collimators to one of the securing means, respectively, and for simultaneously removing the plurality of collimators from the securing means and simultaneously bringing the plurality of collimators out of the opening of the scintillation camera.

2. A scintillation camera system according to claim 1, wherein said scintillation camera system includes at least one rail extending away from the opening in a direction substantially normal to the opening, and the carrier including first wheel means for rolling on a surface, the surface supporting the scintillation camera system, and second wheel means for rolling on the rails, the plurality of collimators being moved by the carrier means such that each collimator moves in a level plane associated with the position of the corresponding securing means.

3. A scintillation camera system according to claim 1, further comprising means for guiding the carrier means to the opening of the scintillation camera.

4. A scintillation camera system according to claim 1, wherein the scintillation camera further includes:
   at least one pin provided on each of the collimators; and
   a guide groove formed in each of the securing means, the guide grooves engaging with the pins to guide the collimator to a predetermined position in the securing means.

5. A scintillation camera system according to claim 1, further comprising means for adjusting a position of the collimators, the position being relative to the securing means.

6. A scintillation camera system according to claim 5, wherein said adjusting means includes:
   means, arranged on the carrier means, for supporting the collimators movably in the direction of gravity; and
   means for lifting the collimators by a predetermined amount when the collimators begin attaching to the securing means.

7. The scintillation camera system according to claim 6, wherein the predetermined amount is a distance which enables the collimators to attach to the securing means.

8. A scintillation camera system according to claim 6, wherein said support means includes sub-supporting means for supporting the collimators movably in a vertical, horizontal and rotating directions such that when the collimators begin attaching to the securing means, the collimators can be moved in the vertical, horizontal and rotating directions to adjust the positions of the collimators relative to the corresponding securing means.

9. A scintillation camera system according to claim 8, wherein the sub-supporting means includes:
   a first block attached to the carrier means;
   a second block movable relative to the first block and supporting a base of each of the collimators; and
   slider members, interposed between the first and second blocks, for enabling the collimators to move in the vertical, horizontal and rotating directions to adjust the positions of the collimators relative to the corresponding securing means.

10. A scintillation camera system according to claim 6, wherein the lifting means includes an area of the securing means where the collimators begin to attach to the securing means, the area being tapered, in a direction substantially normal to the opening of the scintillation camera, to lift the collimators when the collimators begin attaching to the securing means.

11. A scintillation camera system according to claim 1, wherein the scintillation camera comprises means for rotating the detectors around the object.

12. A scintillation camera system according to claim 1, wherein the scintillation camera comprises means for non-rotatably supporting the detectors.

13. A scintillation camera system according to claim 1, wherein the carrier means comprises means for storing the collimators.

14. A scintillation camera system comprising:
   a scintillation camera comprising:
      three detectors collectively forming a triangle-shaped opening for allowing an object such as a human to be inserted into the scintillation camera;
      three collimators corresponding to the three detectors; and
      means for securing the three collimators to the three detectors simultaneously; and
   carrier means, movable toward the triangle-shaped opening, for simultaneously inserting the three collimators into the triangle-shaped opening and for simultaneously attaching the three collimators to the securing means.

* * * * *